United States Patent [19]
Gardner et al.

[11] Patent Number: 5,621,369
[45] Date of Patent: Apr. 15, 1997

[54] FLEXIBLE MAGNET

[76] Inventors: Harris L. Gardner, Cranston, R.I.;
William H. Gardner, heir, c/o 3428 Weymouth Ct., Marietta, Ga. 30062

[21] Appl. No.: 529,613

[22] Filed: Sep. 18, 1995

[51] Int. Cl.$^6$ .................................................. H01F 7/02
[52] U.S. Cl. .................... 335/302; 5/906; 335/303
[58] Field of Search .................... 335/302–306; 600/9, 12, 15; 5/906

[56] References Cited

U.S. PATENT DOCUMENTS

| | | | |
|---|---|---|---|
| 4,391,270 | 7/1983 | Uragami | 600/15 |
| 5,147,447 | 9/1992 | Takeshita et al. | 75/246 |
| 5,214,404 | 5/1993 | Yamaguchi et al. | 335/302 |

*Primary Examiner*—Lincoln Donovan
*Attorney, Agent, or Firm*—Barlow & Barlow, Ltd.

[57] ABSTRACT

A flexible magnetic sheet is made of a rubbery synthetic material in which magnetic ferrite particles have been embedded and which one surface of the sheet has a grid pattern of ridges and depressions. The magnetic material is magnetized so that one pole is one each surface. The magnetic lines of force are generated substantially in a plane.

3 Claims, 1 Drawing Sheet

FLEXIBLE MAGNET

BACKGROUND OF THE INVENTION

The present invention relates generally to a magnetic materials and in particular to a flexible magnetic sheet which may be used therapeutically.

It has been known in the past to employ magnetic therapy and to apply ferrite wafers to certain parts of the body. It is felt that this promotes blood circulation and has certain other therapeutic properties. An example of magnetic material for therapeutic use is seen in U.S. Pat. No. 5,214,404 where the magnetic material is embedded in a mattress and the magnetic poles alternate in crests. Flexible magnets have also been known in which a ferrite is embedded into a plastic-type material and during manufacture is magnetized. Such flexible magnets of which I am aware can be magnetized with multiple poles in an almost infinite variety of ways to achieve different objectives. For example, two poles each side, one pole each side, and multiple poles on one side. I have discovered that if the flexible sheet is altered in configuration by stamping the plastic material to form a grid of ridges and depressions that the flux density of the material is greatly increased and a multi-directional field is created.

SUMMARY OF THE INVENTION

The normal flat flexible sheet magnet is improved upon by altering the sheet, which is substantially a flat body of magnetic particles, in which the particles are magnetized to form a north pole on one surface and a south pole on the opposite surface. By taking one of the surfaces and providing a plurality of valleys and hills in a grid pattern, the pattern preferably being a grid of polygons and, more particularly, pyramidal polygons.

BRIEF DESCRIPTION OF THE DRAWINGS

The novel features which are characteristic of the present invention are set forth in the appended claims. However, the inventions preferred embodiments, together with further objects and attendant advantages, will be best understood by reference to the following detailed description taken in connection with the accompanying drawings in which:

DETAILED DESCRIPTION OF THE PREFERRED EMBODIMENT

Figure 1:
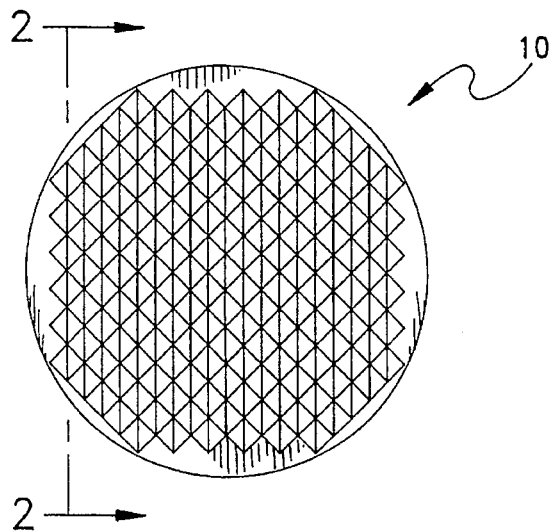
FIG. 1 is top plan view of a flexible body of magnetic particles.
Figure 2:
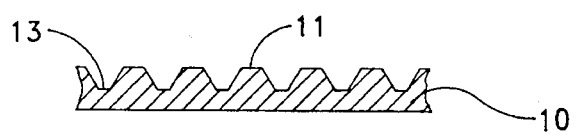
FIG. 2 is an enlarged partial cross-section taken on lines 2—2 of FIG. 1.
Figure 3A:
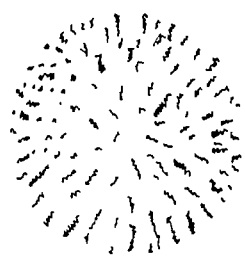
FIG. 3A is a representation of iron filings laid over the material of my invention showing the effect of the magnetic lines of force and FIG. 3B represents a prior art flat sheet.
Figure 3B:

The magnetic material is a plastic sheet 10 which may have a thickness of approximately $1/16$ inch (and 0.15 cm). The sheet may be made in a variety of outline shapes and, for convenience as illustrated in FIG. 1, is seen as a round circle. The material is stamped to a depth to leave approximately $1/10,000$ inch thickness on one face as seen in FIG. 2, where, in the first embodiment, the impression does not completely go through the body but goes substantially therethrough and forms, as seen in FIG. 1, a grid having a plurality of ridges 11 and depressions 13. The depressions, for convenience sake, are being made in the form of a pyramid.

The flexible sheet is a plastic material which has been molded to contain magnetizable particles of ferrite. The plastic sheet can be made from a natural or synthetic rubber or from a silicone rubber and are magnetized by means of a strong magnetic field during the process of manufacture. The sheet is formed with a unipolar face so that a north pole is on one surface and a south pole is on the other surface. The poles are arranged perpendicular to the plane of the sheet and the sheets are formed so that they have a flux density in the order of 1600 Gauss to 2500 Gauss. It has also been found practical to coat the sheet once it is formed with the ridges and valleys with a vacuum deposit of aluminum.

Figure 4:
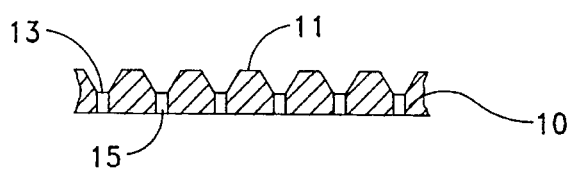
FIG. 4 is a partial cross-section of a modified form.

With reference to FIG. 4, apertures are formed at the base of the depressions that even further increases the magnetic field that is dispersed by the sheet. A configuration of this type is useful for filtering some contaminates from fluids.

It would be appreciated by those skilled in the art that various changes and modifications can be made to the illustrated embodiments without departing from the spirit of the present invention. All such modifications and changes are intended to be covered by the appended claims.

What is claimed is:

1. A substantially flat body of magnetic particles of ferrite material embedded therein, said particles being magnetized to form N poles on one surface and S poles on the opposite surface, one surface having a plurality of valleys and hills in a pattern consisting of a grid of polygon depressions.

2. A body as in claim 1 wherein the polygons are pyramidal.

3. A substantially flat body of magnetic particles of ferrite material embedded therein, said particles being magnetized to form N poles on one surface and S poles on the opposite surface, one surface having a plurality of valleys and hills in a pattern, said valleys having apertures therein.

\* \* \* \* \*